United States Patent [19]
De Lacharriere et al.

[11] Patent Number: 5,803,095
[45] Date of Patent: Sep. 8, 1998

[54] PERMANENT WAVE COMPOSITIONS COMPRISING SUBSTANCE P/CGRP ANTAGONISTS

[75] Inventors: Olivier De Lacharriere, Paris; Geneviève Loussouarn, Clichy; Lionel Breton, Versailles, all of France

[73] Assignee: Société L'Oréal S.A., Paris, France

[21] Appl. No.: 739,480

[22] Filed: Oct. 28, 1996

[30] Foreign Application Priority Data

Oct. 26, 1995 [FR] France ..................... 95 12654

[51] Int. Cl.⁶ .......................................... A45D 7/04
[52] U.S. Cl. .................... 132/204; 132/202; 132/203; 132/200; 424/70.2
[58] Field of Search .................... 132/200, 202, 132/203, 204, 205, 286; 424/62, 70.1, 70.2, 70.4, 70.5, 70.51, 70.6, 274; 8/127.51, 127.6, 160

[56] References Cited

U.S. PATENT DOCUMENTS

| | | | |
|---|---|---|---|
| 2,719,814 | 10/1955 | Haefele | 132/204 |
| 4,313,933 | 2/1982 | Yamazaki | 132/204 |
| 4,363,815 | 12/1982 | Yu et al. | 424/274 |
| 4,947,878 | 8/1990 | Crews et al. | 132/203 |
| 5,437,860 | 8/1995 | Jarvis et al. | 132/202 |

FOREIGN PATENT DOCUMENTS

| | | |
|---|---|---|
| 0235783 | 9/1987 | European Pat. Off. . |
| 0237870 | 9/1987 | European Pat. Off. . |
| 0461526 | 12/1991 | European Pat. Off. . |
| 0624572 | 11/1994 | European Pat. Off. . |
| 0625350 | 11/1994 | European Pat. Off. . |
| 2707486 | 1/1995 | France . |
| 2718351 | 10/1995 | France . |
| 3535351 | 4/1987 | Germany . |
| 3610394 | 10/1987 | Germany . |
| 4336838 | 5/1995 | Germany . |

OTHER PUBLICATIONS

Neuroscience, vol. 48, No. 4, 1992, pp. 963–968, XP000575623, T.L. Buckley et al.
British Journal of Pharmacology, vol. 110, No. 2, Oct. 1993, pp. 772–776, XP000563605, K. Jane Escott et al.
British Journal of Pharmacology, vol. 104, No. 3, 1991, pp. 738–742, XP002007864, S.R. Hughes et al.

*Primary Examiner*—Gene Mancene
*Assistant Examiner*—Pedro Philogene
*Attorney, Agent, or Firm*—Burns, Doane, Swecker & Mathis, L.L.P.

[57] ABSTRACT

Cosmetic compositions, well suited for the permanent deformation of keratinous fibers, for example permanent waves for topical application to human hair, comprise at least one reducing agent and/or at least one oxidizing agent other than a peroxide or cresol, at least one of reducing and/or oxidizing agents normally eliciting a skin irritating side effect, and an effective skin irritant-attenuating/eliminating amount of at least one substance P antagonist and/or at least one CGRP antagonist, in a physiologically acceptable medium therefor.

25 Claims, 2 Drawing Sheets

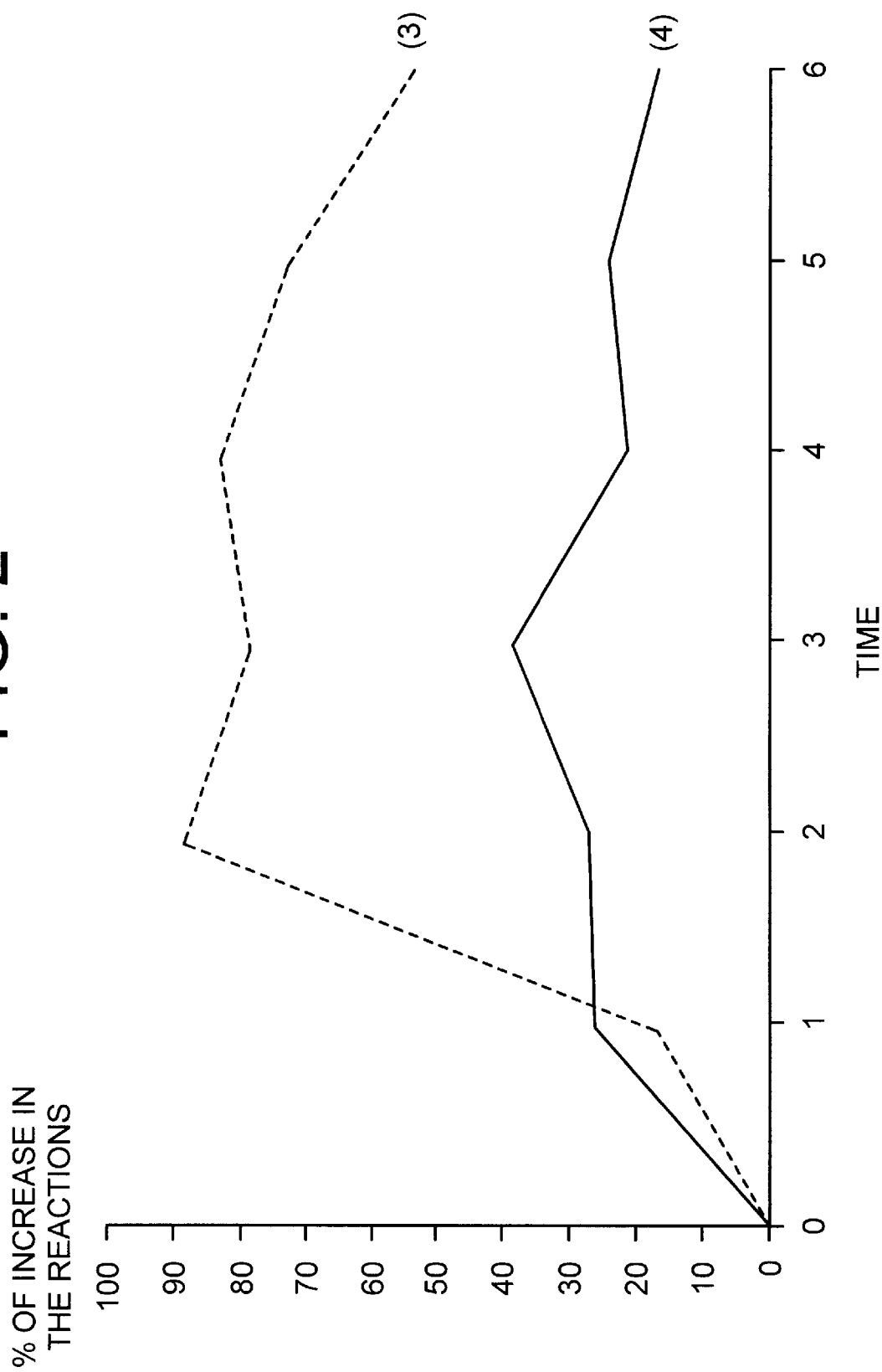

PERMANENT WAVE COMPOSITIONS COMPRISING SUBSTANCE P/CGRP ANTAGONISTS

BACKGROUND OF THE INVENTION

1. Technical Field of the Invention

The present invention relates to novel compositions of matter, in particular novel cosmetic compositions, and more especially novel compositions for the permanent deformation of keratinous fibers comprising at least one substance P antagonist and/or at least one CGRP antagonist, for decreasing, indeed eliminating, the irritant effects of the normally irritating active agents typically contained in such compositions.

2. Description of the Prior Art

It is known to this art that the most usual technique for obtaining permanent hair deformation, hereinafter referred to as a "permanent wave", entails, in a first step, an opening of the —S—S-disulfide bonds of keratin (cystine) using a composition containing a reducing agent (reduction stage) and then, after having rinsed the hair which has thus been treated, in reconstituting, in a second step, the said disulfide bonds by applying an oxidizing composition (oxidation stage, also known as fixing stage) on the hair which has been placed under tension beforehand (perming rods, curlers, and other means), to ultimately impart the desired shape to the hair.

This technique thus makes it possible, without distinction, to carry out either waving of the hair, or its straightening, or its decrimping. The new shape imparted to the hair by a chemical treatment such as above is eminently durable over time and is especially resistant to the effects of water or to washes carried out with a shampoo, in contrast to simple conventional techniques for non-permanent deformation, such as setting.

The reducing compositions which can be used for carrying out the first stage of a permanent wave operation generally contain, as reducing agents, sulfites, bisulfites, alkylphosphines or, preferably, thiols. Among the latter, those commonly employed are cysteine and derivatives thereof, cysteamine and derivatives thereof, thiolactic acid and esters thereof, or thioglycolic acid and esters thereof, especially glyceryl monothioglycolate.

As regards the oxidizing compositions necessary for carrying out the fixing stage, most commonly used, in actual practice, are compositions based on hydrogen peroxide or on alkali metal bromate.

Certain reducing and oxidizing agents and certain adjuvants and additives used for permanent waves can cause irritation and/or feelings of discomfort (for example pins and needles, inflammation or itching) and this skin-irritant effect is experienced, in particular by individuals who have sensitive scalps.

Indeed, certain individuals experience a greater reactivity of the scalp than others. In particular, they respond to certain products, such as hair dyes, permanent waves or surfactants. These individuals, in addition to the clinical signs indicated above, have a tendency to respond more strongly to certain inducement tests which are targeted at reproducing these clinical signs. Among these tests, the assignee hereof has developed the capsaicin test and the monoethanolamine test.

The capsaicin test is described in FR-A-94/05537, assigned to the assignee hereof.

The monoethanolamine test entails preparing an aqueous solution containing 10% of monoethanolamine, in pouring 3 ml of this solution onto a cotton pad, in applying this cotton pad 10 times to the tested areas of the scalp and in evaluating the clinical signs which appear 30 seconds, 2 minutes, 5 minutes, 10 minutes and 15 minutes after application. These signs are essentially subjective signs (smarting, tingling, pins and needles, itching or inflammation), optionally in combination with an erythema.

SUMMARY OF THE INVENTION

It has now unexpectedly and surprisingly been determined that formulating substance P antagonists and/or CGRP antagonists into permanent-wave compositions makes it possible to obtain a preventive and/or curative effect on the irritation due to the irritant compounds normally present in permanent-wave compositions.

Substance P is a polypeptide chemical species developed and released by nerve endings. It is a member of the tachykinin family. Substance P is implicated, in particular, in pain transmission, in diseases of the central nervous system, such as anxiety and schizophrenia, in respiratory and inflammatory diseases, in gastrointestinal diseases, in rheumatic diseases and in certain dermatological diseases, such as eczema.

CGRP (peptide derived from the calcitonin gene: Calcitonin Gene Related Peptide) is a polypeptide chemical species developed and released by a nerve ending. CGRP is implicated, in particular, in respiratory and inflammatory diseases, in allergic diseases and in certain dermatological diseases, such as eczema or prurigo.

It was hitherto unknown to formulate substance P or CGRP antagonists in combination with compounds present in permanent waves and, in particular, reducing and/or oxidizing agents, for the purpose of removing or diminishing the irritant and/or discomfort effect normally caused by such compounds.

A formulation containing cresols and strontium chloride for increasing the antibacterial and antimicrobial properties of such cresols is described in FR-M-5394. However, it is neither described nor suggested that the strontium chloride can, by itself alone, decrease or indeed eliminate symptoms such as irritation, pain, itching or smarting caused by any disease nor decrease or indeed eliminate the same symptoms elicited by an irritant product.

Thus, the present invention features novel compositions, in particular novel cosmetic compositions, which comprise, in a physiologically acceptable medium (vehicle, diluent or carrier), at least one antagonist selected from among substance P antagonists and CGRP antagonists and at least one active agent eliciting an irritant side effect, said active agent eliciting an irritant side effect comprising a reducing agent and/or an oxidizing agent other than a peroxide.

The compositions according to the invention are in particular, compositions for the permanent deformation of keratinous fibers and, especially, compositions for the permanent deformation or "waving" of human hair.

This invention also features compositions for the permanent deformation of keratinous fibers which comprise, in a medium appropriate for permanent deformation, at least one reducing agent and/or at least one oxidizing agent, and since the reducing and/or oxidizing agent elicits a skin-irritating side effect, the composition additionally comprises at least one antagonist selected from among substance P antagonists and CGRP antagonists.

This invention also features the use of monoethanolamine for formulating a composition useful for the determination of sensitive scalps.

The substance P or CGRP antagonist can be applied to keratinous fibers before and/or during and/or after the reduction and/or oxidation stages.

Accordingly, the present invention also features a process for the treatment of keratinous fibers, in particular hair, for the purpose of obtaining a permanent deformation of these fibers, and comprising the following stages:

(i) applying a reducing composition to the keratinous fibers composition, said keratinous fibers having been placed under mechanical tension either before, during or after this application of the reducing composition, (ii) once the reducing composition has taken effect, rinsing the keratinous fibers, (iii) applying an oxidizing composition to the keratinous fibers, (iv) releasing the mechanical tension before or after the stage (iii), (v) optionally rinsing the keratinous fibers, (vi) applying to the keratinous fibers a composition containing at least one antagonist from among substance P antagonists and CGRP antagonists, during at least one of the stages (i) to (v) and/or after at least one of these stages (i) to (v).

In one embodiment of the invention, the various compositions are packaged separately in the form of a kit, in any arrangement well known to this art.

Thus, this invention also features a kit for the treatment of keratinous fibers, in particular of hair, for the purpose of obtaining a permanent deformation of these fibers, comprising a first composition containing a reducing agent and a second composition containing an oxidizing agent, the two compositions, intended to be applied one after the other to the keratinous fibers, being packaged separately, at least one of these compositions containing an antagonist selected from among substance P antagonists and CGRP antagonists.

This invention also features a kit for the treatment of keratinous fibers, in particular of hair, for the purpose of obtaining a permanent deformation of these fibres, comprising a first composition containing a reducing agent, a second composition containing an oxidizing agent and a third composition containing an antagonist selected from among substance P antagonists and CGRP antagonists, the three compositions, intended to be applied one after the other to the keratinous fibers, being packaged separately.

BRIEF DESCRIPTION OF THE FIGURES

FIG. 2 contains the results of a test which plots the time (expressed from 0 to 6) on the absisa as a function of the mean of the percentage increase in the reactions on the ordinate. The dotted curve (3) is that obtained with the placebo, and the continuous-line curve (4) is that obtained with the lotion according to the invention.

Figure 1:
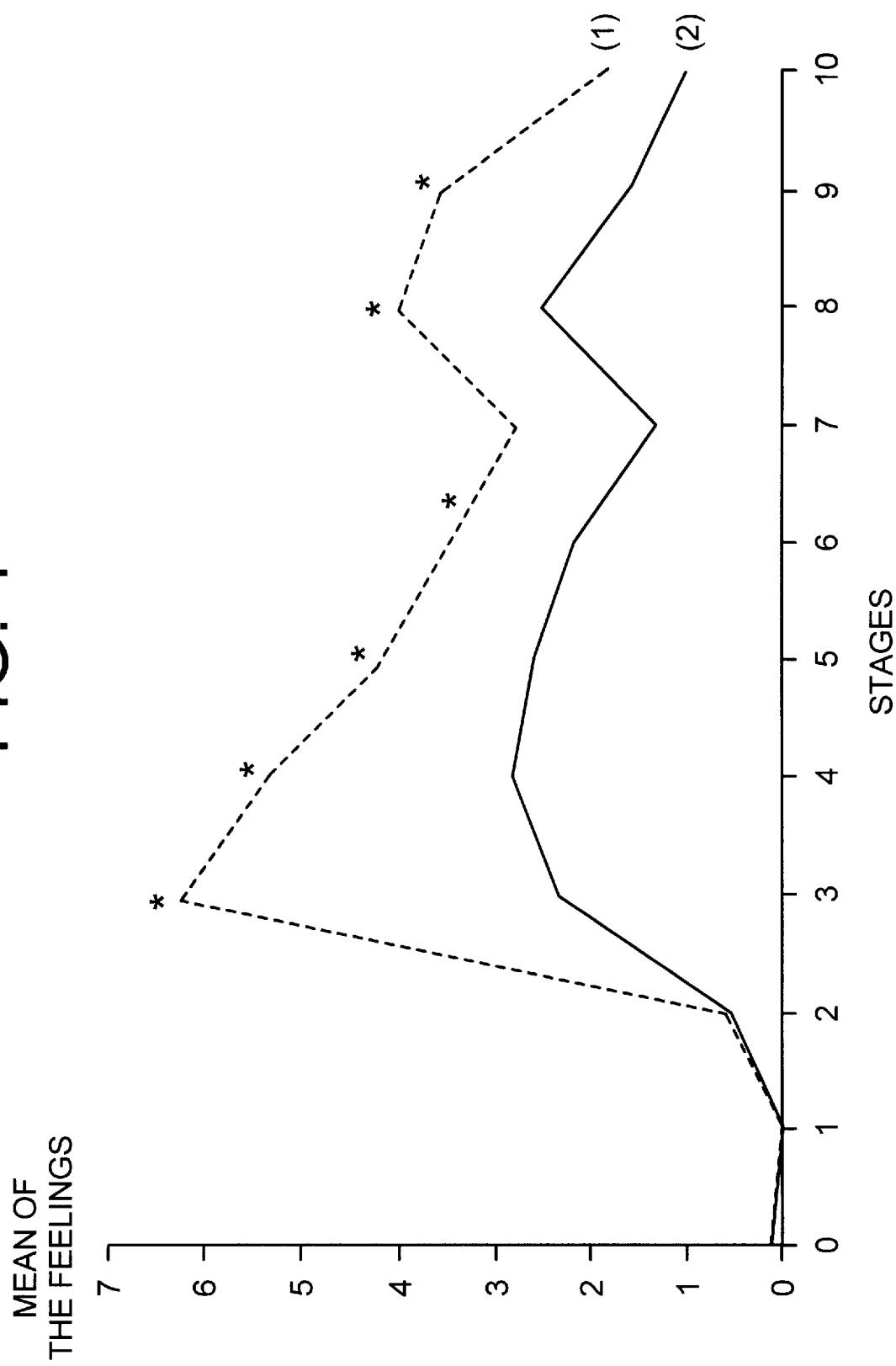
FIG. 1 contains the results of a test which blots the permanent-wave stages (1 to 10) on the absisa as a function of the mean of the feelings of discomfort on the ordinate, these feelings being evaluated from 0 to 7 (no unpleasant feelings at 0, and great discomfort at 7). The dotted curve (1) is that obtained with the placebo, and the continuous-line curve (2) is that obtained with the lotion according to the invention.

DETAILED DESCRIPTION OF BEST MODE AND SPECIFIC/PREFERRED EMBODIMENTS OF THE INVENTION

More particularly according to the present invention, for a substance to be recognized as a substance P antagonist, it must elicit an antagonist pharmacological activity with respect to substance P, namely, induce a coherent pharmacological response in at least one of the two following tests:

(a) the antagonist substance must decrease the extravasation of the plasma through the vascular wall induced by capsaicin or by an antidromic nerve stimulation, or, alternatively;

(b) the antagonist substance must cause inhibition of the contraction of smooth muscles induced by the administration of substance P.

The substance P antagonist can, in addition, have a selective affinity for tachykinin NK1 receptors.

The substance P antagonist of the invention can be functional or receptorial, i.e., inhibit the synthesis and/or the release of substance P, or prevent its binding and/or modulate its effect. It can be selected from among compounds known as substance P antagonists, in particular peptides, non-peptide derivatives, and more specifically those comprising a nitrogen-containing, sulfur-containing or oxygen-containing heterocycle, or nitrogen-containing compounds comprising a nitrogen atom bonded directly or indirectly to a benzene ring. It can also be selected from among salts of monovalent, divalent or trivalent metals and from extracts of plant and/or bacterial origin.

Suitable substance P antagonist peptides according to the invention thus include sendide and spantide II. Also suitable are the peptides described in U.S. Pat. No. 4,472,305, U.S. Pat. No. 4,839,465, EP-A-101,929, EP-A-333,174, EP-A-336,230, EP-A-394,989, EP-A-443,132, EP-A-498,069, EP-A-515,681, EP-A-517,589, WO-A-92/22569 and GB-A-2,216,529.

The non-peptide substance P antagonists which can be used according to the invention are, in particular, heterocyclic compounds, in particular nitrogen-containing, sulfur-containing or oxygen-containing heterocyclic compounds, or compounds comprising a nitrogen atom bonded directly or indirectly to one or a number of benzene rings. Exemplary nitrogen-containing heterocyclic compounds include those described in EP-A-360,390, EP-A-429,366, EP-A-430,771, EP-A-499,313, EP-A-514,273, EP-A-514,274, EP-A-514,275, EP-A-514,276, EP-A-520,555, EP-A-528,495, EP-A-532,456, EP-A-545,478, EP-A-558,156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099 or WO-A-93/09116. Advantageously, the compound comprising at least one nitrogen-containing heterocycle is a 2-tricyclyl-2-aminoethane derivative, a spirolactam derivative, a quinuclidine derivative, an azacyclic derivative, an aminopyrrolidine derivative, a piperidine derivative, an aminoazaheterocycle or an isoindole derivative.

Exemplary of other heterocyclic compounds are the oxygen-containing or sulfur-containing heterocyclic compounds, such as furan derivatives, benzofuran derivatives, thiophene derivatives and benzothiophene derivatives, optionally comprising nitrogen-containing substituents, such as the heterocyclic compounds described in U.S. Pat. No. 4,931,459, U.S. Pat. No. 4,910,317 and EP-A-299,457 and more especially alkoxy- and/or aryloxytetrazolylbenzofurancarboxamides or alkoxy- and/or aryloxytetrazolylbenzothiophenecarboxamides.

And exemplary compounds containing a nitrogen atom bonded directly or indirectly to a benzene ring include those described in EP-A-522,808, WO-A-93/01165 and WO-A-93/10073. Especially representative are the ethylenediamine derivatives, such as N,N'-bisdi(3,5-dimethylbenzyl) ethylenediamine or N,N'-bisdi(3,5-dimethoxybenzyl) ethylenediamine; these compounds are described as synthetic intermediates in the WO-A-93/11338, assigned to the assignee hereof.

The salts of monovalent, divalent or trivalent metals which are suitable for use according to this invention as substance P antagonists can be cobalt salts; salts of elements from column IIA of the Periodic Table, in particular beryllium, magnesium or alkaline earth metal salts, in particular strontium, calcium and barium salts; lanthanide salts, in particular lanthanum and gadolinium salts; yttrium salts; zinc salts; manganese salts; copper salts; rubidium salts or lithium salts.

These salts are advantageously, for example, chlorides, carbonates, bicarbonates, borates, nitrates, acetates, hydroxides, sulfates, persulfates or glycerophosphates, as well as salts of α-hydroxy acids or salts of fruit acids (citrate, tartrate, lactate or malate) or, alternatively, salts of amino acids (aspartate, arginate, glucocholate or fumarate) or salts of fatty acids (palmitate, oleate, caseinate or behenate).

The salt is advantageously a strontium salt and in particular strontium chloride or strontium nitrate.

The extracts of bacterial origin which are suitable per this invention can be extracts from at least one non-photosynthetic filamentous bacterium.

Exemplary extracts of plant origin which can be used in the invention include those originating from *Iris germanica, Iris florentina, Iris pallida, Crocus versicolor, Romulea bulbucodium* or, alternatively, *Gladiolus communis*. More particularly according to the present invention, a plant extract emanating from an Iridacea and preferentially from plant material from *Iris pallida* is employed. Any extraction technique known to this art can be used to prepare the extract contained in the composition according to the invention. Representative are alcoholic extracts, in particular ethanolic extracts, or aqueous/alcoholic extracts. It is also possible to use an extract prepared by the technique described in FR-A-95/02379, assdigned to the assignee hereof.

For a substance to be recognized as a CGRP antagonist, it must exhibit, in particular, the following characteristics:

(a) have an affinity for CGRP receptors and/or (b) have an antagonist pharmacological activity with respect to CGRP, namely, induce a coherent pharmacological response, in particular in one of the following tests:

(i) the antagonist substance must decrease the vasodilation induced by capsaicin and/or (ii) the antagonist substance must cause inhibition of the release of CGRP by sensitive nerve fibres and/or (iii) the antagonist substance must cause inhibition of the contraction of the smooth muscle of the vas deferens induced by CGRP.

Exemplary CGRP antagonists include CGRP 8–37 (sequence of the amino acids 8 to 37 of the terminal end of CGRP) or an anti-CGRP antibody.

In the compositions according to the invention, the substance P or CGRP antagonist is preferably formulated in an amount ranging from 0.000001% to 30% by weight with respect to the total weight of the composition and, in particular, in an amount ranging from 0.0001% to 10% by weight with respect to the total weight of the composition.

The substance P or CGRP antagonist acts essentially on the reducing and/or oxidizing agents which exhibits an irritant effect, the non-irritant agents being, moreover, present in the compositions according to the invention in order to enable the desired deformation to be attained.

In the first stage (i) of the treatment according to the invention, a reducing composition containing at least one active agent appropriate for the reduction of the disulfide bonds of keratin is applied to the keratinous fibers. This application can be made before, during or after the usual stage of placing the keratinous fibers under tension. The substance P or CGRP antagonist can be present in the reducing composition, or in a composition applied to the keratinous fibers before or after the reduction stage.

The usual stage of placing the keratinous fibers, in particular the hair, under tension in a shape corresponding to the final desired hair shape (curls, for example) can be carried out by any appropriate means, in particular mechanical means, known per se for maintaining hair under tension, such as, for example, hair rollers, perming rods and the like.

Exemplary active agents appropriate for the reduction of the disulfide bonds of keratin include the sulfites, bisulfites, alkylphosphines and, preferably, thiols. Among the latter, those that are preferred are thioglycolic acid, glyceryl or glycol monothioglycolate, cysteamine and the $C_1$–$C_4$ acylated derivatives thereof, such as N-acetylcysteamine or N-propionylcysteamine, cysteine, N-acetylcysteine, cysteine esters, such as glyceryl cysteinate, the N-mercaptoalkylamides of sugars, such as N-(2-mercaptoethyl)gluconamide, thiolactic acid and esters thereof, such as glyceryl monothiolactate, 3-mercaptopropionic acid and esters thereof, such as glyceryl 3-mercaptopropionate, thiomalic acid, 2-hydroxy-3-mercaptopropionic acid and esters thereof, such as glyceryl 2-hydroxy-3-mercaptopropionate, pantetheine, thioglycerol, the sulfites or the bisulfites of an alkali metal or alkaline earth metal, the N-(mercaptoalkyl)-ω-hydroxyalkylamides described in EP-A-354,835 and the N-mono- or N,N-dialkyl-4-mercaptobutyramides described in EP-A-368,763, the aminomercaptoalkylamides described in EP-A-432,000, the derivatives of N-(mercaptoalkyl)succinamic acids or of N-(mercaptoalkyl)succinimides described in EP-A-465,342, the alkylaminomercaptoalkylamides described in EP-A-514, 282, the mixture of 2-hydroxypropyl thioglycolate and of 2-hydroxy-1-methylethyl thioglycolate described in FR-A-2,679,448 or the N-(mercaptoalkyl)alkanediamides described in EP-A-653,202.

More preferred is thioglycolic acid, thiolactic acid, cysteine and derivatives thereof, cysteamine and derivatives thereof, 3-mercaptopropionic acid and their esters or their salts, in particular glyceryl monothioglycolate.

These active agents can be used alone or in admixture.

When thioglycolic acid, thiolactic acid, 3-mercaptopropionic acid, 2-hydroxy-3-mercaptopropionic acid, cysteine or cysteamine or one of their salts or of their derivatives is employed as a reducing agent, the pH of the combined composition according to the invention preferably ranges from 6 to 11.5 and more preferably from 7 to 10.

When the esters of thioglycolic acid or of thiolactic acid or of 3-mercaptopropionic acid, of cysteine or of 2-hydroxy-3-mercaptopropionic acid are employed as a reducing agent, the pH of the combined composition according to the invention preferably ranges from 5 to 10 and more preferably from 6 to 9.

The reducing agents indicated above are generally present at a concentration which can range from 1% to 20% by weight with respect to the total weight of the reducing composition.

The pH values of the reducing compositions can be adjusted conventionally by addition of basifying agents, for the purpose of making the reducing agents more effective. These basifying agents can be selected, for example, from among sodium hydroxide, ammonia, monoethanolamine, diethanolamine, triethanolamine, isopropanolamine, 1,3-propanediamine, an alkali metal or ammonium carbonate or bicarbonate, a primary, secondary or tertiary amine carbonate or bicarbonate or an organic carbonate, such as guanidine carbonate, it being possible, of course, for all of these compounds to be used alone or in admixture.

The substance P or CGRP antagonist makes it possible, in addition, to reduce the irritant effect of certain of these basifying agents.

The reducing composition can be provided in the form of a lotion, which may or may not be thickened, of a cream, of a gel or in any other appropriate form and can contain additives and adjuvants known for their use in reducing compositions for the permanent deformation of hair.

The reducing composition can also be of the exothermic type.

The reducing composition can also contain a solvent, such as, for example, ethanol, propanol or isopropanol or, alternatively, glycerol, at a maximum concentration of 20% with respect to the total weight of the composition.

When the subject compositions are intended for a hair straightening or decrimping operation, the reducing composition is preferably in the form of a thickened cream, so as to keep the hair as stiff as possible. These creams are produced in the form of "heavy" emulsions, for example based on glyceryl stearate, glycol stearate, self-emulsifiable waxes, fatty alcohols, and the like.

It is also possible to use liquids or gels containing thickening agents such as carboxyvinyl polymers or copolymers which "stick" the hair and maintain it in the smooth position during the setting time.

Finally, the compositions can also be in the so-called "self-neutralizing" or, alternatively, "self-regulated" form and, in this instance, the reducing agents are combined with at least one disulfide known for its use in a self-neutralizing reducing composition for a permanent wave.

Exemplary such known disulfides include dithioglycolic acid, dithioglycerol, cystamine, N,N'-diacetylcystamine, cystine, pantethine, and the disulfides of N-(mercaptoalkyl)-ω-hydroxyalkylamides described in EP-A-354,835, the disulfides of N-mono- or N,N-dialkyl-4-mercaptobutyramides described in EP-A-368,763, the disulfides of aminomercaptoalkylamides described in EP-A-432,000, the disulfides of derivatives of N-(mercaptoalkyl)succinamic acids or of N-(mercaptoalkyl)succinimides described in EP-A-465,342, the disulfides of alkylaminomercaptoalkylamides described in EP-A-514,282 and the disulfides of N-(mercaptoalkyl) alkanediamides described in EP-A-653,202. These disulfides are generally present in a molar ratio of 0.5 to 2.5, and preferably of 1 to 2, with respect to the reducing agent.

Prior to carrying out the following rinsing stage (ii), it is advisable, conventionally, to allow the keratinous fibers, to which the reducing composition has been applied, to rest for a few minutes, generally between 2 and 40 minutes and preferably between 5 and 30 minutes, to permit the reducing agent ample time to act properly on the keratinous fibers. This waiting phase is generally carried out while allowing the treated keratinous fibers to rest while exposed to the air (room temperature), but it can also be carried out at a higher temperature. During this waiting phase, care is taken that the keratinous fibers do not dry out completely and remain damp up to the time of carrying out the following stage.

In the second stage (ii) of the process, the keratinous fibers impregnated with the reducing composition are thus carefully rinsed with an aqueous composition to which a substance P antagonist and/or a CGRP antagonist have optionally been added.

In a third stage (iii), an oxidizing composition is then applied to the keratinous fibers, thus rinsed, for the purpose of fixing the new shape imparted to the keratinous fibers, it being possible for this oxidizing composition to also contain a substance P antagonist and/or CGRP antagonist.

The mechanical means (rollers, perming rods and the like), which maintained the keratinous fibers under tension and in the desired shape throughout the treatment, can be removed from the keratinous fibers either before or after the fixing stage.

The oxidizing composition contains an oxidizing agent which can be selected from among hydrogen peroxide, an alkali metal bromate, a persalt, a chlorite or a polythionate or mixture thereof, such as a mixture of alkali metal bromate and of a persalt. Well suited, for example, is potassium bromate, sodium perborate or sodium chlorite.

The hydrogen peroxide concentration advantageously varies from 1 to 10 volumes, but is preferably 8 volumes. The alkali metal bromate concentration generally ranges from 1% to 12% and the persalt concentration from 0.1% to 15% by weight with respect to the total weight of the oxidizing composition.

The pH of the oxidizing composition generally ranges from 2 to 10.

The oxidizing composition can contain cosmetic additives and adjuvants well known for this type of composition.

As in the case of the application of the reducing composition, the hair to which the oxidizing composition has been applied is next, conventionally, maintained in a resting or waiting phase which lasts a few minutes, generally between 3 and 30 minutes and preferably between 5 and 15 minutes.

The vehicle of the reducing and oxidizing compositions according to the invention is preferably water or a water/alcoholic solution of a lower alcohol, such as ethanol, isopropanol or butanol.

The hydrogen peroxide can be stabilized, for example with phenacetin, acetanilide or mono- and trisodium phosphates or with 8-hydroxyquinoline sulfate.

The oxidizing composition can also contain basifying or acidifying agents, preservatives, sequestering agents or opacifiers.

Lastly, the keratinous fibers impregnated with the oxidizing composition are carefully rinsed, generally with water to which a substance P antagonist and/or a CGRP antagonist have optionally been added.

Hair is ultimately provided which exhibits the desired shaping, without the existence of irritation or discomfort.

The amounts of the various constituents of the compositions according to the invention are those conventionally used in the fields under consideration.

In order to further illustrate the present invention and the advantages thereof, the following specific examples are given, it being understood that same are intended only as illustrative and in nowise limitative.

EXAMPLE 1

Permanent-wave composition

A. Reducing composition:

| | |
|---|---|
| (a) thioglycolic acid | 9.2 g |
| (b) sodium carbonate | 1 g |
| (c) monoethanolamine | q.s. pH 8.5 |
| (d) cocoylamidopropylbetaine/glyceryl monolaurate (25/5) mixture marketed under the trademark "Tegobetaine HS" by Goldschmidt containing 30% of active material | 0.3 g AM |
| (e) strontium chloride | 5 g |
| (f) demineralized water | q.s. for 100 g |

B. Oxidizing composition:

| | |
|---|---|
| (g) hydrogen peroxide | q.s. for 8 volumes |
| (h) citric acid | q.s. pH 3 |
| (i) demineralized water | q.s. for 100 g |

The procedure employed was as follows: the reducing composition was applied to the wound and damp hair (diameter of the rollers: 9 mm) and a plastic cap was then placed over the hair, followed by a wait of 15 minutes. The cap was then removed and the hair was rinsed. The oxidizing composition was then applied to the hair; it was permitted to act for 10 minutes and the rollers were then removed. The hair was then rinsed with water and finally dried.

EXAMPLE 2

The same reducing composition was prepared as in Example 1, but with the 5 g of strontium chloride being replaced by 0.05 g of Spantide II. The oxidizing composition was the same as in Example 1.

EXAMPLE 3

The same reducing composition was prepared as in Example 1, but with the 5 g of strontium chloride being replaced by 0.5 g of CGRP 8–37. The oxidizing composition was the same as in Example 1.

EXAMPLE 4

The same reducing composition was prepared as in Example 1 and an oxidizing composition was prepared which additionally comprised 5 g of an *Iris pallida* extract prepared in the following manner:

Undifferentiated *Iris pallida* cells cultured in vitro under axenic conditions were recovered, after culturing in an Erlenmeyer flask or in a fermenter, by filtering through a 50 μm sieve. 27.5 ml of demineralized water were added to 55 g of fresh material thus obtained. The entire mixture was milled with a Turax at 24,000 R/min for 1 minute at 4° C. (ice bath). The milled material was centrifuged at 4° C. The supernatant was filtered at 0.22 μm (sterilizing filtration). The extract thus prepared was stored at 4° C. It contained approximately 15 g of solids per liter.

EXAMPLE 5

Permanent-wave composition

Composition containing substance P antagonist (A):

(a) Aqueous/alcoholic lotion (water/ethanol: 90/10) containing 6.3% of strontium chloride.

Reducing composition (B):

| | |
|---|---|
| (b) thioglycolic acid | 9.4 g |
| (c) aqueous ammonia containing 20% of ammonia | 11.5 g |
| (d) ammonium bicarbonate | 5.8 g |
| (e) ETA pentasodium salt as a 40% aqueous solution | 0.2 g |
| (f) cocoylbetaine | 0.45 g |
| (g) polyethylene glycol 6 EO laurate (Laurynol 13 marketed by Interchimie) | 0.09 g |
| (h) tetramethylhexamethylenediamine/ 1,3-dichloropropylene poly-condensate as a 60% aqueous solution | 2.0 g |
| (i) diammonium dithioglycolate as a 48% aqueous solution | 7.5 g |
| (j) oleyl alcohol oxyethylenated 10 EO | 1.5 g |
| (k) demineralized water | q.s. for 100 g |

Oxidizing composition (C):

| | |
|---|---|
| (l) hydrogen peroxide containing 200 volumes | 4.8 g |
| (m) stabilizers | q.s. |
| (n) acidifying agent | q.s. for pH 3 |
| (o) demineralized water | q.s. for 100 g |

To produce the permanent wave, the composition (A) containing the substance P antagonist was first applied and then the procedure described in the preceding examples was carried out.

A test was carried out in order to demonstrate, with respect to the placebo (A'), the soothing effect of the composition (A) applied before the permanent wave. The test was carried out on 13 subjects.

The placebo (A') was an aqueous/alcoholic solution (water/ethanol: 90/10).

The test entailed applying, before the permanent wave, the lotion (A) to one half of the head and the lotion (A') to the other half of the head and in evaluating the feelings of discomfort (smarting, itching or burning sensations) before and during the permanent-wave stages.

The results of the test are set forth in FIG. 1, which plots the permanent-wave stages (1 to 10) on the abscissa as a function of the mean of the feelings of discomfort on the ordinate, these feelings being evaluated from 0 to 7 (no unpleasant feelings at 0 and great discomfort at 7). The dotted curve (1) is that obtained with the placebo and the continuous-line curve (2) is that obtained with the lotion according to the invention.

The stages were as follows:
1. Application per half of the head of the lotion (A) or (A');
2. Winding of the hair on rollers;
3. Application of the composition (B);
4. 2 minutes after application of the composition (B);
5. 5 minutes after application of the composition (B);
6. 10 minutes after application of the composition (B);
7. Rinsing;
8. Application of the composition (C);
9. 5 minutes after application of the composition (C);
10. Rinsing.

FIG. 1 demonstrates a marked decrease in the feelings of discomfort when the treatment of the hair was preceded by the application of the composition (A) according to the invention containing a substance P antagonist.

EXAMPLE 6

Monoethanolamine test

A test was carried out which demonstrated the soothing effect of a substance P antagonist after induction of a reaction by application of monoethanolamine on 14 subjects having sensitive scalps.

The test entailed first treating the scalp per half of the head either with an aqueous/alcoholic lotion (water/ethanol: 90/10) containing 5% of strontium chloride or with a placebo composed of an aqueous/alcoholic solution (water/ethanol: 90/10), in then applying a 10% aqueous monoethanolamine solution and in then clinically evaluating the feelings of discomfort (smarting, itching or burning sensations) up to 15 minutes after the application of the aqueous monoethanolamine solution.

The results of the test are presented in FIG. 2 which plots the time (expressed from 0 to 6) on the abscissa as a function of the mean of the percentage increase in the reactions on the ordinate. The dotted curve (3) is that obtained with the placebo and the continuous-line curve (4) is that obtained with the lotion according to the invention.

The time on the abscissa corresponds to the following real times:
1. After application of the lotion according to the invention or of the placebo and before application of the monoethanolamine solution;
2. 30 seconds after application of the monoethanolamine solution;
3. 2 minutes after application of the monoethanolamine solution;
4. 5 minutes after application of the monoethanolamine solution;
5. 10 minutes after application of the monoethanolamine solution;
6. 15 minutes after application of the monoethanolamine solution.

FIG. 2 demonstrates a marked decrease in the reactions when the treatment of the hair is preceded by the application of the lotion according to the invention containing a substance P antagonist.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A cosmetic composition of matter suited for the permanent deformation of keratinous fibers, comprising at least one reducing agent and/or at least one oxidizing agent other than a peroxide or cresol, at least one of said reducing and/or oxidizing agents normally eliciting a skin irritating side effect, and an effective skin irritant-attenuating/eliminating amount of at least one substance P antagonist and/or at least one CGRP antagonist, in a physiologically acceptable medium therefor.

2. The cosmetic composition as defined by claim 1, comprising a permanent wave for topical application to human hair.

3. The cosmetic composition as defined by claim 1, comprising at least one substance P antagonist selected from among peptides, compounds which comprise at least one heterocycle, nitrogen-containing compounds which comprise one or more benzene rings, salts of monovalent, divalent or trivalent metals, extracts of plant origin, extracts of bacterial origin, and mixtures thereof.

4. The cosmetic composition as defined by claim 3, said at least one substance P antagonist comprising sendide or spantide II.

5. The cosmetic composition as defined by claim 3, comprising at least one nitrogen-containing heterocyclic compound selected from among 2-tricyclyl-2-aminoethane derivatives, spirolactam derivatives, quinuclidine derivatives, azacyclic derivatives, aminopyrrolidine derivatives, piperidine derivatives, aminoazaheterocycles, isoindole derivatives and mixtures thereof.

6. The cosmetic composition as defined by claim 3, comprising at least one oxygen-containing or sulfur-containing heterocyclic compound selected from among furan derivatives, benzofuran derivatives, thiophene derivatives, benzothiophene derivatives, tetrazolylbenzofurancarboxamides or tetrazolylbenzothiophenecarboxamides, and mixtures thereof.

7. The cosmetic composition as defined by claim 3, comprising at least one ethylenediamine derivative.

8. The cosmetic composition as defined by claim 3, comprising a monovalent, divalent or trivalent metal salt selected from among cobalt, beryllium, magnesium, strontium, calcium, barium, lanthanide, lanthanum, gadolinium, yttrium, zinc, manganese, copper, rubidium and/or lithium chlorides, carbonates, bicarbonates, borates, nitrates, acetates, hydroxides, sulfates, persulfates, glycerophosphates, salts of α-hydroxy acids, salts of fruit acids, salts of amino acids and salts of fatty acids, and mixtures thereof.

9. The cosmetic composition as defined by claim 8, comprising a strontium salt.

10. The cosmetic composition as defined by claim 3, comprising an Iridacea extract.

11. The cosmetic composition as defined by claim 1, comprising at least one CGRP antagonist selected from among CGRP 8–37, anti-CGRP antibodies and mixtures thereof.

12. The cosmetic composition as defined by claim 1, said at least one antagonist comprising from 0.000001% to 30% by weight with respect to the total weight thereof.

13. The cosmetic composition as defined by claim 12, said at least one antagonist comprising from 0.0001% to 10% by weight with respect to the total weight thereof.

14. The cosmetic composition as defined by claim 1, comprising at least one reducing agent selected from among sulfites, bisulfites, alkylphosphines, thiols and mixtures thereof.

15. The cosmetic composition as defined by claim 1, comprising at least one reducing agent selected from among cysteine and derivatives thereof, cysteamine and derivatives thereof, thiolactic acid and esters thereof, thioglycolic acid and esters thereof, and mixtures thereof.

16. The cosmetic composition as defined by claim 1, comprising at least one oxidizing agent selected from among alkali metal bromates, persalts, chlorites, polythionates, and mixtures thereof.

17. The cosmetic composition as defined by claim 1, comprising at least one oxidizing agent selected from among sodium perborate, potassium bromate, sodium chlorite, and mixtures thereof.

18. The cosmetic composition as defined by claim 1, said physiologically acceptable medium comprising water or a mixture of water and an organic solvent.

19. The cosmetic composition as defined by claim 1, further comprising at least one basifying agent, acidifying agent, preservative, sequestering agent, opacifier, or mixture thereof.

20. A cosmetic composition of matter suited for the permanent deformation of keratinous fibers, comprising at least one reducing agent and/or at least one oxidizing agent other than a cresol, at least one of said reducing and/or oxidizing agents normally eliciting a skin irritating side effect, and an effective skin irritant-attenuating/eliminating amount of at least one substance P antagonist and/or at least one CGRP antagonist, in a physiologically acceptable medium therefor.

21. The cosmetic composition as defined by claim 20, comprising a permanent wave for topical application to human hair.

22. A process for the permanent deformation of keratinous fibers, comprising (i) topically applying a reducing agent to said keratinous fibers, said fibers being placed under mechanical tension either before, during or after application of said reducing agent, (ii) after said reducing agent has elicited the desired response, rinsing said keratinous fibers, (iii) topically applying an oxidizing agent to said keratinous fibers, (iv) releasing said mechanical tension before or after said stage (iii), (v) optionally rinsing said keratinous fibers, and (vi) topically applying at least one substance P antagonist and/or CGRP antagonist to said keratinous fibers either during and/or after at least one of said stages (i) to (v).

23. The process as defined by claim 22, wherein said keratinous fibers comprise viable human hair.

24. A kit for the permanent deformation of keratinous fibers, wherein the constituents of the kit upon combination result in a cosmetic composition of matter suited for the permanent deformation of keratinous fibers and wherein said constituents are packaged in at least two separate packages, a first package confining said at least one reducing agent and a second package confining said at least one oxidizing agent, at least one of said packages also confining at least a fraction of said at least one substance P antagonist and/or CGRP antagonist.

25. A kit for the permanent deformation of keratinous fibers, wherein the constituents of the kit upon combination result in a cosmetic composition of matter suited for the permanent deformation of keratinous fibers and wherein said constituents are packaged therein in at least three separate packages, a first package confining said at least one reducing agent, a second package confining said at least one oxidizing agent, and a third package confining at least a fraction of said at least one substance P antagonist and/or CGRP antagonist.

* * * * *

UNITED STATES PATENT AND TRADEMARK OFFICE
CERTIFICATE OF CORRECTION

PATENT NO. : 5,803,095
DATED : September 8, 1998
INVENTOR(S) : Olivier DE LACHARRIERE et al.

It is certified that error appears in the above-identified patent and that said Letters Patent is hereby corrected as shown below:

At Column 4, line 8, change "cause inhibition" to --reduce inhibition--.

Signed and Sealed this

Twenty-fourth Day of October, 2000

Attest:

Q. TODD DICKINSON

*Attesting Officer*     *Director of Patents and Trademarks*